United States Patent [19]
Kilpatrick et al.

[11] Patent Number: 4,891,108
[45] Date of Patent: Jan. 2, 1990

[54] PROCESS FOR PREPARING TETRAHALOPYRIDINES

[75] Inventors: Steven C. Kilpatrick; Billy J. Watson, both of Angleton, Tex.

[73] Assignee: The Dow Chemical Company, Midland, Mich.

[21] Appl. No.: 27,993

[22] Filed: Mar. 17, 1987

Related U.S. Application Data

[63] Continuation of Ser. No. 768,292, Aug. 22, 1985, abandoned.

[51] Int. Cl.$^4$ ............................................. C07D 211/72
[52] U.S. Cl. ................................. 204/157.71; 546/345
[58] Field of Search ..................... 546/345; 204/157.71

[56] References Cited

U.S. PATENT DOCUMENTS

| | | | |
|---|---|---|---|
| 3,186,944 | 6/1965 | Johnston et al. | 546/345 |
| 3,297,556 | 1/1967 | Boudakian et al. | 546/345 |
| 3,303,196 | 2/1967 | Corran | 546/345 |
| 3,420,833 | 1/1969 | Taplin | 546/345 |
| 3,538,100 | 11/1970 | Smith | 546/345 |
| 3,555,032 | 1/1971 | Johnston | 546/345 |
| 3,732,230 | 5/1973 | Brewer | 546/345 |
| 4,256,894 | 3/1981 | Dietsche et al. | 546/345 |
| 4,281,135 | 7/1981 | Perettie et al. | 546/345 |
| 4,515,953 | 5/1985 | Marinak et al. | 546/345 |
| 4,681,945 | 7/1987 | Humphreys et al. | 546/345 |

OTHER PUBLICATIONS

Suschitzky, Polychloroaromatic Compounds, pp. 225–227 and 439–440, (1980).

Primary Examiner—Alan L. Rotman
Assistant Examiner—Robert C. Whittenbaugh
Attorney, Agent, or Firm—D. Wendell Osborne

[57] ABSTRACT

Symmetrical or 2,3,5,6-tetrahalopyridine is prepared by reacting 3,5-dihalopyridine in the liquid phase with chlorine or bromine while heating and irradiating the reactants with ultraviolet light. The reaction may be carried out with or without a chlorinated solvent. For example, 2,3,5,6-tetra-chloropyridine is prepared selectively from 3,5-dichloropyridine by chlorination at 140°–150° C. under ultraviolet light for 44 hours.

21 Claims, No Drawings

PROCESS FOR PREPARING TETRAHALOPYRIDINES

RELATED U.S. APPLICATION DATA

This application is a continuation of Ser. No. 768,292, filed Aug. 22, 1985, now abandoned.

TECHNICAL FIELD

The present invention relates to the preparation of chloro substituted pyridines and more particularly, to the preparation of 2,3,5-trichloropyridine and 2,3,5,6-tetrachloropyridine. Still more particularly, the present invention relates to the preparation of 2,3,5-trichloropyridine and 2,3,5,6-tetrachloropyridine from 3,5-dichloropyridine through the chlorination thereof under ultraviolet light.

BACKGROUND OF THE INVENTION 2,3,5-Trichloropyridine is useful as an intermediate compound for the preparation of various pesticides for the control of mites, insects, bacteria and fungal organisms. Several processes have been used in the past for the preparation of 2,3,5-trichloropyridine.

U.S. Pat. No. 4,108,856 discloses a method for preparing 2.3.5-trichloropyridine by the vapor phase chlorination of 3,5-dichloropyridine at a temperature in the range from 300° C. to 460° C. 2,3,5,6-tetrachloropyridine is also produced during that reaction. The amount of 2,3,5,6-tetrachloropyridine, however, is appreciably smaller than the amount of 2,3,5-trichloropyridine product.

U.S. Pat. No. 4,127,575 discloses a process for preparing 2,3,5-trichloropyridine by the oxidation of 2,3,5-trichloro-6-hydrazinopyridine with or without 2,3,5-trichloro-4-hydrazinopyridine by an alkaline hypochlorite in the presence of a reaction medium at temperatures in the range of from room temperature to the boiling point of the reaction mixture. U.S. Pat. No. 4,379,938 discloses a method for preparing 2,3,5-trichloropyridine by reacting 3,5-dichloro-2-pyridone in a solvent with phosgene in the presence of an N,N-disubstituted formamide at a temperature in the range from 30° C. to 105° C.

2,3,5,6 or symmetrical tetrachloropyridine is used for the preparation of herbicides and pesticides. Numerous processes have been employed in the past for the preparation of 2,3,5,6-tetrachloropyridine.

Some processes utilize the chlorination of other chloropyridines for the production of 2,3,5,6-tetrachloropyridine. U.S. Pat. No. 3,186,994 discloses a method for preparing 2,3,5,6-tetrachloropyridine by reacting chlorine and 3,5-dichloro-2-(trichloromethyl)-pyridine or 2,3,5-trichloro-6-(trichloromethyl)pyridine at temperatures of at least 160° C. U.S. Pat. Nos. 3,538,100 and 4,281,135 disclose processes for the preparation of 2,3,5,6-tetrachloropyridine by reacting 2,6-dichloropyridine with chlorine in the presence of a catalyst. In U.S. Pat. No. 4,256,894, 2,3,5,6-tetrachloropyridine is produced by reacting chlorine with 2-chloro-6-(trichloromethyl)pyridine in the presence of a catalyst at temperatures ranging from 160° C. to 220° C. and pressures ranging from 15 psig to 220 psig.

Other processes for the production of 2,3,5,6-tetrachloropyridine disclosed in the past utilize pentachloropyridine as one of the reactants. U.S. Pat. No. 3,993,654 discloses a process for preparing 2,3,5,6-tetrachloropyridine by heating pentachloropyridine in an aqueous medium under pressure, with agitation, in the presence of zinc and hydrogen chloride. U.S. Pat. No. 4,259,495 discloses a process for the preparation of 2,3,5,6-tetrachloropyridine by dechlorinating pentachloropyridine in an ester solvent in the presence of an ammonium salt of an inorganic or an organic acid. U.S. Pat. No. 4,321,389 discloses a process for the production of 2,3,5,6-tetrachloropyridine by transhalogenating pentachloropyridine by a bromide salt in a polar, aprotic solvent at a temperature from about 100° C. to about 140° C. followed by selectively debrominating by hydrogen in the presence of a noble metal catalyst and an acid acceptor. Pentachloropyridine is also used as a reactant in a process disclosed in U.S. Pat. No. 4,322,538 for producing 2,3,5,6-tetrachloropyridine by reacting the pentachloropyridine with iodide ions and a proton donor in a polar, aprotic solvent at a temperature from about 100° C. to 200° C.

Other processes for the production of 2,3,5,6-tetrachloropyridine are disclosed in U.S. Pat. No. 4,127,575 wherein 2,3,5,6-tetrachloropyridine is produced by reacting tetrachloro-4-hydrazinopyridine with alkaline hypochlorite in a reaction medium at temperatures from room temperature to the boiling point of the reaction mixture, and in U.S. Pat. No. 4,327,216 wherein 2,3,5,6-tetrachloropyridine is produced by reacting trichloroacetyl chloride with acrylonitrile in an inert organic solvent in the presence of a catalyst.

The prior art discloses only one method for the production of appreciable amounts of 2,3,5-trichloropyridine and 2,3,5,6-tetrachloropyridine from 3,5-dichloropyridine, a by-product of reactions carried out for the preparation of other chlorinated pyridines. That method is the vapor phase chlorination disclosed in the aforementioned U.S. Pat. No. 4,108,856. One disadvantage of that method is that it is carried out at elevated temperatures in the range from 300° C. to 400° C. and that it involves the handling of gaseous materials. Another disadvantage is that it appears to favor the formation of 2,3,5-trichloropyridine over 2,3,5,6-tetrachloropyridine.

While past attempts to chlorinate 3,5-dichloropyridine in the liquid phase resulted in a chloropyridine yield strongly favoring the formation in undesirable 2,3,4,5 or unsymmetrical tetrachloropyridine, the present invention discloses a novel and economical process for the preparation of 2,3,5-trichloropyridine and/or 2,3,5,6-tetrachloropyridine from 3,5-dichloropyridine that is carried out at a low temperature with the chlorinated pyridine reactant and products being in the liquid phase. Furthermore, the present invention discloses a novel process that favors the formation of 2,3,5,6-tetrachloropyridine over 2,3,5-trichloropyridine.

These and other advantages of the present invention will become apparent from the following description.

SUMMARY OF THE INVENTION 2,3,5-Trichloropyridine and 2,3,5,6-tetrachloropyridine are manufactured by chlorinating 3,5-dichloropyridine in the liquid phase with or without the presence of a diluent, under ultraviolet radiation. The reaction is carried out at a temperature in the range from 60° C. to the boiling point temperature of the chloropyridine reactant when diluent is utilized and at a temperature at which the chloropyridine reactant is in the liquid phase when diluent is not used.

DETAILED DESCRIPTION OF THE INVENTION

According to the present invention, 3,5-dichloropyridine in the liquid phase reacts with chlorine in the vapor phase while the mixture is irradiated with ultraviolet light to produce 2,3,5-trichloropyridine and/or 2,3,5,6-tetrachloropyridine. The chlorination reaction produces initially 2,3,5-trichloropyridine which in turn is further chlorinated to produce 2,3,5,6-tetrachloropyridine. Therefore, under the process disclosed herein, one may produce not only 2,3,5,6-tetrachloropyridine from 3,5-dichloropyridine, but also, one may produce 2,3,5-trichloropyridine from 3,5-dichloropyridine and 2,3,5,6-tetrachloropyridine from 2,3,5-trichloropyridine.

Irradiation with ultraviolet light promotes the chlorination of the appropriate sites for the formation of the 2,3,5,6 or symmetrical tetrachloropyridine from 3,5-dichloropyridine during the liquid phase chlorination thereof. In the past, attempts to chlorinate liquid 3,5-dichloropyridine in the absence of ultraviolet light resulted in a chloropyridine yield strongly favoring the formation of 2,3,4,5 or unsymmetrical tetrachloropyridine. While it is preferred to use a source of ultraviolet light with relatively high intensity, it will be seen from the examples that follow that an ordinary ultraviolet light source such as a mercury vapor lamp would be sufficient to promote the chlorination process disclosed herein.

The 3,5-dichloropyridine reactant used in this process may be of reagent grade purity or in a mixture with other chlorinated pyridines or pyridine-related compounds. Therefore, the present invention may be used to convert 3,5-dichloropyridine that is the by-product of a chlorination reaction before the 3,5-dichloropyridine is separated from the other by-products. It is apparent, however, that the presence of other chlorinated compounds may reduce the rate of the reaction and may increase the formation of undesirable by-products including heavies. An example of a chlorination reaction in which 3,5-dichloropyridine is a by-product is the one disclosed in U.S. Pat. No. 3,993,654.

The invention in question may be carried out with or without a chlorinated solvent, preferably carbon tetrachloride. The use of a solvent is beneficial for solubilizing the reacting 3,5-dichloropyridine which would be otherwise in a solid phase under certain conditions, i.e., under its melting point.

The reaction in question may be carried out under various temperature conditions depending on whether a solvent is used. More particularly, when a solvent is used to solubilize the reactant, the reaction may be carried out at a temperature from 60° C. to the boiling point temperature of the chlorinated pyridine reactants that correspond to the particular operating pressure. If the reaction is carried out without the presence of a solvent, the reaction could be carried out at a temperature from the melting point temperature of the chlorinated pyridine reactant to the boiling point temperature thereof that corresponds to the particular operating pressure. While the reaction temperatures may be within the aforementioned wide ranges, it should be understood that the reaction rate increases as the reaction temperature increases.

As regards the pressure conditions of the process disclosed herein, the reaction may be carried out at a pressure from atmospheric to approximately 200 psig. The reaction rate increases as the reaction pressure increases. The cost of the equipment, however, used under pressurized conditions is higher and therefore, a pressure could be chosen within the aforementioned range by balancing the reaction rate requirements and the economics.

The reaction in question is relatively slow, sometimes requiring a residence time exceeding 40 hours to obtain a desirable conversion of 3,5-dichloropyridine. Therefore, it is more practical to conduct the reaction in question in a batch mode. Pure 3,5-dichloropyridine or 3,5dichloropyridine in a chlorinated solvent is introduced into a batch reactor and is heated to the appropriate reaction temperature. Chlorine gas is sparged into the heated chloropyridine at a slow rate for a sufficiently long period of time while irradiating the reaction mixture with ultraviolet light. Following the termination of the chlorination process, the product is removed and the desired components are separated via well-known distillation and isomer separation techniques. As discussed hereinafter, 3,5-dichloropyridine hydrochloride is one of the by-products formed during the process in question. This by-product reacts with iron, and therefore, it is necessary that the reactor used in the process and the other equipment contacting such by-product be made or plated with material other than iron such as glass or ceramic.

While theoretically the stoichiometric requirements of the reaction dictate the utilization of two moles of chlorine gas to chlorinate one mole of 3,5-dichloropyridine to 2,3,5,6-tetrachloropyridine, in the batch operation described hereinabove, one should use more than one mole of chlorine per mole of 3,5-dichloropyridine requiring chlorination. The amount of chlorine used depends on the mixing of the reactants, concentration of the reactants when in a mixture, and other factors. Specifically, the amount of chlorine used may range from 1 to 50 moles per mole of 3,5-dichloropyridine requiring conversion. The excess chlorine used may be recovered by separating it from the chlorine/hydrogen chloride off-gas.

While the reaction in question is relatively slow, if the reaction is carried out for a sufficient period of time and if the amount of chlorine added is adequate, more than 99% of the 3,5-dichloropyridine may be converted, the primary product being tetrachloropyridine isomers wherein more than 97% of such isomer would be 2,3,5,6-tetrachloropyridine, otherwise known as symmetrical tetrachloropyridine.

An undesirable characteristic of the invention in question is that the reaction described hereinabove generates an appreciable amount of 3,5-dichloropyridine hydrochloride which in turn forms heavies in the form of chlorinated bipyridyls. These heavy compounds plug the reactor and the related equipment and the disposal thereof is very difficult. The plugging problem may be eliminated by carrying out the reaction in the presence of water. Water solubilizes the 3,5-dichloropyridine hydrochloride whereby the formation of the heavy chlorinated bipyridyls is minimized.

While the detailed description of the invention hereinabove and the examples that follow refer to the chlorination of 3,5-dichloropyridine to 2,3,5-trichloropyridine and 2,3,5,6-tetrachloropyridine, it should be understood that the present invention discloses the liquid phase fluorination of 3,5-difluoropyridine to 2,3,5-trifluoropyridine and/or 2,3,5,6-tetrafluoropyridine and the liquid phase bromination of 3,5-dibromopyridine to 2,3,5-tribromopyridine and/or 2,3,5,6-tetrabromopyridine through irradiation with ultraviolet light.

The following examples further illustrate the invention but are not to be construed as limitations on the scope of the process contemplated herein.

EXAMPLE 1

Reagent grade 3,5-dichloropyridine (27.6 g or 0.19 mole) was added to a 50 ml glass reaction flask having a round bottom and being equipped with a water-cooled condenser and a thermometer with a temperature controller. The dichloropyridine was heated to 140° C. in a hot bath. Anhydrous chlorine gas was then spurged into the liquid dichloropyridine at an approximate flow rate of 0.1 moles per hour for 15 hours while irradiating the reaction mixture with a 160 watt mercury vapor lamp acting as an ultraviolet source. The reaction mixture was sampled at approximately 7 hours and at completion. The samples were analyzed by gas chromatography to determine the composition. The results are shown in Table A.

TABLE A

| Reaction Time (Hours) | 0.0 | 7.3 | 14.9 |
|---|---|---|---|
| Reaction Temperature (°C.) | 140 | 140 | 140 |
| Reactants and Products Component Analysis (Wt %) | | | |
| 3,5-dichloropyridine | 99.53 | 52.42 | 12.79 |
| 2,3,5-trichloropyridine | 0.01 | 42.49 | 69.41 |
| Tetrachloropyridine Isomers | 0.00 | 1.06 | 4.93 |
| Pentachloropyridine | 0.00 | 0.09 | 0.26 |
| Heavies | 0.00 | 3.94 | 12.49 |
| Tetrachloropyridine Isomer Component Analysis | | | |
| 2,3,4,5 | 0.00 | 5.04 | 2.41 |
| 2,3,4,6 | 0.00 | 0.00 | 0.00 |
| 2,3,5,6 | 0.00 | 94.96 | 97.59 |

EXAMPLE 2

The by-product mixture of a commercial application of the process disclosed in U.S. Pat. No. 3,993,654 was vacuum distilled in a twenty tray Oldershaw column to remove the diluent from the mixture. The residue mixture (80.48 g) composed primarily of dichloropyridines, trichloropyridines, and tetrachloropyridines was added to a 100 ml glass reaction flask having a round bottom and being equipped as described in Example 1. The residue mixture was heated to 140° C. Chlorine gas was then sparged into the heated residue mixture at an approximate rate of 0.1 moles per hour for 44 hours. During the first 21.5 hours, the reaction mixture was irradiated with a 160 watt mercury vapor lamp acting as an ultraviolet source. During the remainder reaction time, the 160 watt lamp was replaced with a 275 watt lamp and the reaction temperature was raised to 150° C. Samples were taken periodically throughout the run and were analyzed by gas chromatography to determine the composition. Results of the sampling in the analysis thereof are shown in Table B.

TABLE B

| Reaction Time (Hours) | 0.0 | 6.8 | 12.2 | 16.8 |
|---|---|---|---|---|
| Reaction Temperature (°C.) | 140 | 140 | 140 | 140 |
| Reactants and Products Component Analysis (Wt %) | | | | |
| 3,5-dichloropyridine | 13.68 | 5.54 | 2.81 | 0.36 |
| 2,5-dichloropyridine | 0.94 | 0.68 | 0.42 | 0.22 |
| 2,3,5-trichloropyridine | 37.60 | 40.83 | 38.98 | 36.84 |
| Tetrachloropyridine Isomers | 32.61 | 34.59 | 36.93 | 41.33 |
| Pentachloropyridine | 0.02 | 0.07 | 0.17 | 0.19 |
| Heavies | 0.67 | 3.30 | 6.40 | 6.67 |
| Tetrachloropyridine Isomer Component Analysis | | | | |
| 2,3,4,5 | 0.00 | 0.00 | 0.00 | 0.00 |
| 2,3,4,6 | 4.45 | 4.13 | 3.69 | N.A. |
| 2,3,5,6 | 95.55 | 95.87 | 96.31 | N.A. |
| Reaction Time (Hours) | 21.6 | 27.6 | 33.5 | 44.0 |
| Reaction Temperature (°C.) | 140 | 150 | 150 | 150 |
| Reactants and Products Component Analysis (Wt %) | | | | |
| 3,5-dichloropyridine | 0.07 | 0.04 | 0.05 | 0.05 |
| 2,5-dichloropyridine | 0.09 | 0.00 | 0.00 | 0.00 |
| 2,3,5-trichloropyridine | 30.92 | 18.21 | 12.12 | 5.03 |
| Tetrachloropyridine Isomers | 45.88 | 58.27 | 59.10 | 65.95 |
| Pentachloropyridine | 0.32 | 0.72 | 1.19 | 1.86 |
| Heavies | 9.27 | 10.06 | 14.74 | 15.25 |
| Tetrachloropyridine Isomer Component Analysis | | | | |
| 2,3,4,5 | 0.00 | 0.00 | 0.00 | 0.00 |
| 2,3,4,6 | 2.82 | 2.17 | 2.14 | 1.69 |
| 2,3,5,6 | 97.18 | 97.83 | 97.86 | 98.31 |

EXAMPLE 3

A mixture containing 29.9 grams 3,5-dichloropyridine and 513.2 grams carbon tetrachloride solvent was added to a glass reaction flask being equipped with a water cooled condenser and a thermometer with a temperature controller. The mixture was heated to 60° C. in a hot bath. Anhydrous chlorine gas was then sparged into the liquid mixture at a controlled rate for about 5.2 hours and then another rate for 17.7 hours until 380 grams chlorine had been added over the 22.9 hours, while irradiating the reaction mixture with a 100 watt mercury vapor lamp acting as an ultraviolet source. 5 grams of water were added to the mixture shortly after beginning in a single addition. The reaction mixture was sampled at completion. The samples were analyzed to determine the composition. The results are shown in Table C.

TABLE C

| Reaction Time (Hours) | 0.0 | 22.9 |
|---|---|---|
| Reaction Temperature (°C.) | 60 | 60 |
| Reactants and Products Component Analysis (Wt %) | | |
| 3,5-dichloropyridine | 5.50 | 0.02 |
| 2,3,5-trichloropyridine | 0.00 | 3.61 |
| Tetrachloropyridine Isomer | 0.00 | 1.67 |
| Pentachloropyridine | 0.00 | 0.20 |
| Carbontetrachloride | 94.50 | 94.50 |
| Tetrachloropyridine Isomer Component Analysis | | |
| 2,3,4,5 | 0.00 | 8.18 |
| 2,3,4,6 | 0.00 | 0.00 |

| TABLE C-continued | | |
|---|---|---|
| 2,3,5,6 | 0.00 | 91.82 |

Although the invention is described with respect to specific embodiments and modifications, the details hereof are not to be construed as limitations except to the extend indicated in the following claims.

What is claimed is:

1. A process for preparing 2,3,5,6-tetrachloropyridine which comprises contacting 3,5-dichloropyridine with chlorine to obtain a mixture and irradiating with ultraviolet light and heating the mixture at a temperature of between 60° C. and the boiling point of 3,5-dichloropyridine, in the liquid phase, for a sufficient amount of time to form a product of which at least about 92 percent of the tetrachloropyridines produced is 2,3,5,6-tetrachloropyridine.

2. A process according to claim 1 wherein the irradiated mixture further comprises a chlorinated solvent.

3. A process according to claim 1 wherein the solvent is carbon tetrachloride.

4. A process according to claim 1 conducted in the absence of substantial amounts of chlorinated solvents.

5. A process according to claim 1 wherein the irradiated mixture further comprises water.

6. A process according to claim 1 wherein the 3,5-dichloropyridine is additionally heated before being contacted with chlorine.

7. A process according to claim 1 wherein the ultraviolet light is provided by at least one mercury vapor lamp.

8. A process for preparing 2,3,5,6-tetrachloropyridine which comprises contacting 2,3,5-trichloropyridine with chlorine to obtain a mixture and irradiating with ultraviolet light and heating the mixture at a temperature of between 60° C. and the boiling point of 2,3,5tri- chloropyridine, in the liquid phase, for a sufficient amount of time to form a product of which at least about 92 percent of the tetrachloropyridines produced is 2,3,5,6-tetrachloropyridine.

9. A process according to the claim 8 wherein the irradiated mixture further comprises a chlorinated solvent.

10. A process according to claim 9 wherein the solvent is carbon tetrachloride.

11. A process according to claim 8 conducted in the absence of substantial amounts of chlorinated solvents.

12. A process according to claim 8 wherein the irradiated mixture further comprises water.

13. A process according to claim 8 wherein the 2,3,5-trichloropyridine is additionally heated before being contacted with chlorine.

14. A process according to claim 8 wherein the ultraviolet light is provided by at least one mercury vapor lamp.

15. A process for preparing 2,3,5-trichloropyridine which comprises contacting 3,5-dichloropyridine with chlorine to obtain a mixture and irradiating with ultraviolet light and heating the mixture at a temperature of between 60° C. and the boiling point of 3,5-dichloropyridine, in the liquid phase, for a sufficient amount of time to form a product of which at least about 92 percent of the trichloropyridines produced is 2,3,5-trichloropyridine.

16. A process according to the claim 15 wherein the irradiated mixture further comprises a chlorinated solvent.

17. A process according to claim 16 wherein the solvent is carbon tetrachloride.

18. A process according to claim 15 conducted in the absence of substantial amounts of chlorinated solvents.

19. A process according to claim 15 wherein the irradiated mixture further comprises water.

20. A process according to claim 15 wherein the 3,5-dichloropyridine is additionally heated before being contacted with chlorine.

21. A process according to claim 15 wherein the ultraviolet light is provided by at least one mercury vapor lamp.

* * * * *